US010258645B2

(12) United States Patent
Goldfarb et al.

(10) Patent No.: US 10,258,645 B2
(45) **Date of Patent: *Apr. 16, 2019**

(54) CITRATE CONTAINING BEVERAGE

(71) Applicants: New York University, New York, NY (US); General Hospital Corporation, Boston, MA (US); The Regents of the University of California, Oakland, CA (US)

(72) Inventors: David S. Goldfarb, Hastings-on-Hudson, NY (US); Brian Eisner, Needham, MA (US); John Asplin, Chicago, IL (US); Marshall L. Stoller, San Francisco, CA (US)

(73) Assignees: New York University, New York, NY (US); General Hospital Corporation, Boston, MA (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/897,344

(22) Filed: Feb. 15, 2018

(65) Prior Publication Data

US 2018/0169144 A1 Jun. 21, 2018

Related U.S. Application Data

(63) Continuation of application No. 15/681,703, filed on Aug. 21, 2017, now Pat. No. 9,895,396, which is a (Continued)

(51) Int. Cl.

*A61K 33/08* (2006.01)
*A23L 2/52* (2006.01)

(Continued)

(52) U.S. Cl.

CPC ................ *A61K 33/08* (2013.01); *A23L 2/52* (2013.01); *A23L 2/66* (2013.01); *A23L 2/68* (2013.01);

(Continued)

(58) Field of Classification Search

None

See application file for complete search history.

(56) References Cited

U.S. PATENT DOCUMENTS 4,966,776 A 10/1990 Pak
4,985,593 A 1/1991 Walsdorf et al.

(Continued)

FOREIGN PATENT DOCUMENTS

CN 1033349 6/1989
CN 1284303 2/2001

(Continued)

OTHER PUBLICATIONS http://www.emedicinehealth.com/drug-potassium_bicarbonate_and_potassium_chloride/article_em.htm; Effervescent Potassium/Chloride, K-Lyte/Cl; Cerner Multum, Inc.; Dec. 9, 2011.

(Continued)

*Primary Examiner* — Robert A Wax
*Assistant Examiner* — Melissa S Mercier
(74) *Attorney, Agent, or Firm* — Hodgson Russ LLP

(57) ABSTRACT

Provided are beverage compositions comprising a urine citrate increasing component and a urine oxalate reducing component. The beverage compositions may be provided in a ready-to-drink form or may be provided in a concentrate form. Also provided are kits comprising the beverage compositions and methods for treating various conditions using the beverage compositions.

8 Claims, 1 Drawing Sheet

Record diet and drink 2.0 L of water
Record diet and drink 2.0 L of water
Record diet and drink 2.0 L of water
24-hour urine collection
Day 1 Day 2 Day 3

Eat Day 1 diet and drink 2.0 L of Ravine
Eat Day 2 diet and drink 2.0 L of Ravine
Eat Day 3 diet and drink 2.0 L of Ravine
24-hour urine collection
Day 1 Day 2 Day 3

Related U.S. Application Data continuation of application No. 15/062,509, filed on Mar. 7, 2016, now Pat. No. 9,737,564, which is a continuation of application No. 14/211,645, filed on Mar. 14, 2014, now Pat. No. 9,278,112.

(60) Provisional application No. 61/793,442, filed on Mar. 15, 2013.

(51) Int. Cl.

| | |
|---|---|
| ***A61K 31/4415*** | (2006.01) |
| ***A61K 31/194*** | (2006.01) |
| ***A23L 2/66*** | (2006.01) |
| ***A23L 2/68*** | (2006.01) |
| ***A61K 45/06*** | (2006.01) |
| ***A61K 33/06*** | (2006.01) |
| ***A23L 33/16*** | (2016.01) |
| ***A23L 33/20*** | (2016.01) |

(52) U.S. Cl.

CPC ............... *A23L 33/16* (2016.08); *A23L 33/20* (2016.08); *A61K 31/194* (2013.01); *A61K 31/4415* (2013.01); *A61K 33/06* (2013.01); *A61K 45/06* (2013.01); *A23V 2002/00* (2013.01)

(56) References Cited

U.S. PATENT DOCUMENTS

| | | | | |
|---|---|---|---|---|
| 5,085,883 | A | 2/1992 | Garleb et al. | |
| 5,108,767 | A | 4/1992 | Mulchandani et al. | |
| 5,438,042 | A | 8/1995 | Schmidl et al. | |
| 7,205,018 | B2 | 4/2007 | Sherwood et al. | |
| 7,781,003 | B2 | 8/2010 | Bailey et al. | |
| 7,897,192 | B2 | 3/2011 | Sherwood et al. | |
| 7,993,690 | B2 | 8/2011 | Murray et al. | |
| 8,147,894 | B2 * | 4/2012 | Euber | A23L 33/40 426/585 |
| 8,216,614 | B2 | 7/2012 | Pak et al. | |
| 9,278,112 | B2 * | 3/2016 | Goldfarb | A23L 2/52 |
| 9,737,564 | B2 * | 8/2017 | Goldfarb | A23L 2/52 |
| 9,895,396 | B2 * | 2/2018 | Goldfarb | A23L 2/52 |
| 2001/0002269 | A1 | 5/2001 | Zhao | |
| 2003/0203072 | A1 | 10/2003 | O'Mahony et al. | |
| 2005/0276839 | A1 | 12/2005 | Rifkin | |
| 2007/0077314 | A1 | 4/2007 | Pak et al. | |
| 2009/0232961 | A1 | 9/2009 | Ichihara et al. | |
| 2012/0128815 | A1 | 5/2012 | Poulos et al. | |

FOREIGN PATENT DOCUMENTS

| | | | |
|---|---|---|---|
| DE | 2252665 | | 9/1987 |
| GB | 1403900 | A | 8/1975 |
| JP | H07501685 | A | 2/1995 |
| JP | 2010527590 | A | 8/2010 |
| WO | 0193831 | | 12/2001 |
| WO | 2012013975 | | 2/2012 |

OTHER PUBLICATIONS http://www.fda.gov/food/guidanceregulation/guidancedocumentsregulatoryinformation/labelingnutrition/ucm064911.htm; Guidance for Industry: A Food Labeling Guide; Food and Drug Administration, Oct. 2009.

http://www.urocit-k.com/; Urocit-K | Potassium Citrate for Kidney Stone Disease; Mission Pharmacal Company, Oct. 2011.

http://www.drugs.com/cdi/klor-con-ef-effervescent-tablets.html; Klor-Con/EF Effervescent Tablets Facts and Comparisons at Drugs.com, Mar. 10, 2011.

http://www.drugs.com/drp/beelith-tablets.html; Beelith Tablets, Jan. 7, 2011.

Grampsas et al., 10-year experience with extra corporeal shockwave lithotripsy in the state of Colorado; J Endourol., Nov. 2000, vol. 14, No. 9, pp. 711-714.

Tiselius, Patients' attitudes on how to deal with the risk of future stone recurrences; UrolRes, Aug. 2006, vol. 34, No. 4, pp. 255-260.

Preminger et al., Prevention of recurrent calcium stone formation with potassium citrate therapy in patients with distal renal tubular acidosis, J. Urol., Jul. 1985, vol. 134, No. 1, pp. 20-23.

Barcelo et al., Randomized double-blind study of potassium citrate in idiopathic hypocitraturic calcium hephrolithiasis, J. Urol., Dec. 1993, vol. 150, No. 6, pp. 1761-1764.

Ettinger et al., Potassium-magnesium citrate is an effective prophylaxis against recurrent calcium oxalate hephrolithiasis, J. Urol. Dec. 1997, vol. 158, No. 6, pp. 2069-2073.

Jehle et al., Effect of potassium citrate on bone density, microarchitecture, and fracture risk in healthy older adults without osteoporosis: a randomized controlled trial, J. Clin. Endocrinol. Metab., Nov. 15, 2012, vol. 98, No. 1, pp. 207-217.

Borghi et al., Urinary volume, water and recurrences in idiopathic calcium nephrolithiasis: a 5-year randomized prospective study, J. Urol. Mar. 1996, vol. 155, No. 3, pp. 839-843.

Hall et al, Risk factors for kidney stones in older women in the southern United States, Am J Med Sci. Jul. 2001, vol. 322, No. 1, pp. 12-18.

Curhan et al., A prospective study of the intake of vitamins C and B6, and the risk of kidney stones in men, J Urol, Jun. 1996, vol. 155, No. 6, pp. 1847-1851.

Curhan et al., Intake of vitamins B6 and C and the risk of kidney stones in women, J Am Soc Nephrol, Apr. 1999, vol. 10, No. 4, pp. 840-845.

Seltzer et al., Dietary manipulation with lemonade to treat hypocitraturic calcium nephrolithiasis, J Urol., Sep. 1996, vol. 156, No. 3, pp. 907-909.

Odvina, Comparative value of orange juice versus lemonade in reducing stone-forming risk, Clin J Am Soc Nephrol., Nov. 2006, vol. 1, No. 6, pp. 1269-1274.

Goodman et al., Effect of two sports drinks on urinary lithogenicity, Urol Res., Feb. 2009, vol. 37, No. 1, pp. 41-46.

Goldfarb et al., Effect of grapefruit juice on urinary lithogenicity, J Urol., Jul. 2001, vol. 166, No. 1, pp. 263-267.

Sumorok et al., Effect of diet orange soda on urinary lithogenicity, Urol Res., Jun. 2012, vol. 40, No. 3, pp. 237-241.

Kang et al., Long-term lemonade based dietary manipulation in patients with hypocitraturic nephrolithiasis, J Urol., Apr. 2007, vol. 177, No. 4, pp. 1358-1362.

Frang, Fifteen-Year Experience With Magurlit in the Treatment of Patients with Uric Acid Calculi, Therapia Hungarica, Jan. 1986, vol. 34, No. 1, pp. 26-34.

Frang, A Comparative Study of 3 Different Citrate Combinations of Litholytic Action, International Urology and Nephrology, Jan. 1978, vol. 10, No. 3, pp. 195-199.

Zongyue, et al., Risk Factors Related to Urolithiasis, Medical Recapitulate, Jan. 30, 2009, vol. 15, No. 2, pp. 220-222.

Qingfiao, et al., Effect of Potassium Citrate on Calcium Oxalate Crystallization Prepared in Lithogenic Urines and Healthy Urines Gel Systems, Journal of Synthetic Crystals, Oct. 30, 2006, vol. 35, No. 5, pp. 1099-1103.

* cited by examiner

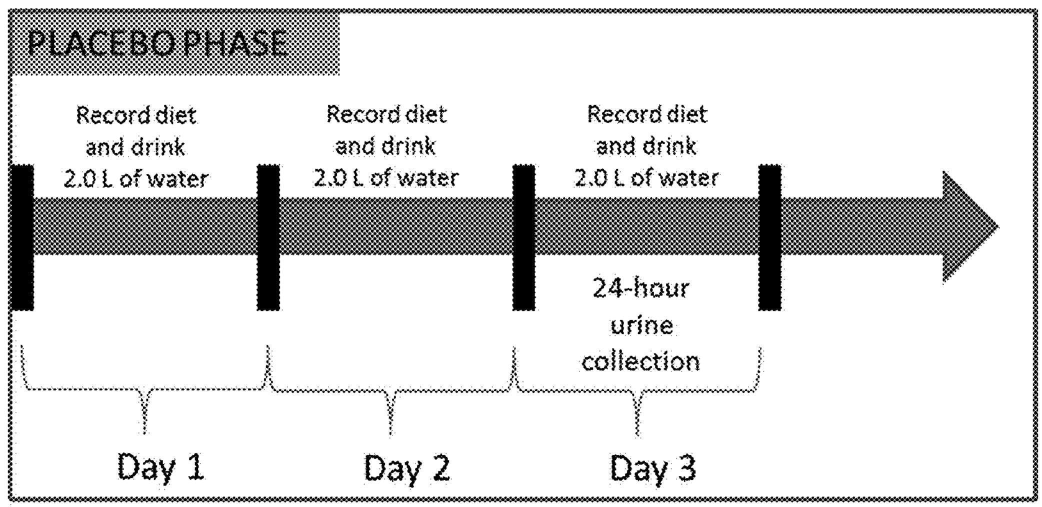
WASHOUT PHASE (4-14 DAYS)
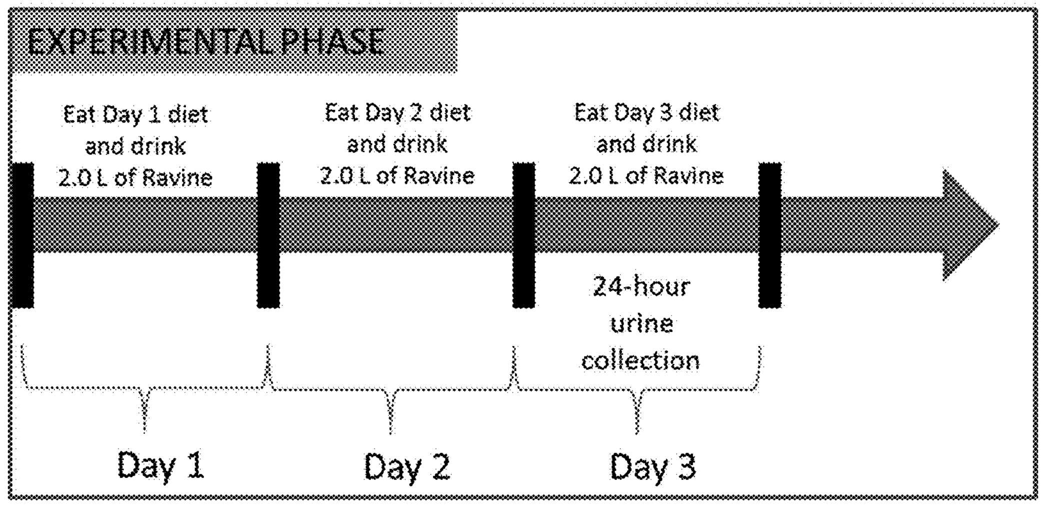

CITRATE CONTAINING BEVERAGE

CROSS-REFERENCE TO RELATED APPLICATIONS

This application is a continuation of U.S. patent application Ser. No. 15/681,703, filed on Aug. 21, 2017, which is a continuation of U.S. patent application Ser. No. 15/062,509, filed on Mar. 7, 2016, (now U.S. Pat. No. 9,737,564), which in turn is a continuation of U.S. patent application Ser. No. 14/211,645, filed on Mar. 14, 2014 (now U.S. Pat. No. 9,278,112), which claims priority to U.S. Provisional application No. 61/793,442, filed on Mar. 15, 2013, the disclosures of each of which are incorporated herein by reference in their entirety.

BACKGROUND OF THE INVENTION

Kidney stones are a common cause of morbidity, with a lifetime worldwide prevalence of 5-10%. In the absence of prevention, recurrence is common, with over 50% of patients having a recurrent stone episode within 5-10 years of their first stone. The most common stone type is calcium oxalate. A second type of stone that may occur is calcium phosphate. Calcium-based stones comprise roughly 80% of all stones. At least 10% of stones are composed of uric acid and about 1% of stones (and 6% of stones in children) are composed of cystine.

Although it is considered that patients are amenable to modifying their eating and drinking habits in preference to taking prescription pills for the prevention of various conditions, there is no beverage currently available that is designed to increase urine citrate and pH, while reducing urinary calcium.

SUMMARY OF THE DISCLOSURE

The present invention is based, in part, on the inventors' surprising and unexpected discovery that beverages made in accordance with the invention and comprising a urine citrate increasing component and a urine oxalate reducing component have improved benefits in the management of kidney stones as compared to prior art compositions. The invention encompasses a beverage comprising a urine citrate increasing component and a urine oxalate reducing component. The invention contemplates beverages to be ready to drink or alternatively reconstituted from powdered mixes, concentrated liquid (concentrate) or tablets.

In a specific embodiment, the urine citrate increasing component comprises sodium citrate, potassium citrate or magnesium citrate, or combinations thereof. In one specific preferred embodiment, the invention provides a beverage comprising sodium citrate, potassium citrate, magnesium citrate, citric acid, pyridoxine and combinations thereof.

In some embodiments, the oxalate reducing component is a magnesium salt. In one specific preferred embodiment, the magnesium salt is magnesium hydroxide.

In other preferred embodiments, the oxalate reducing component is selected from the group consisting of a magnesium, pyridoxine and combinations thereof.

In some embodiments, the beverage of the invention comprises citrate, magnesium and pyridoxine.

In some embodiments, the beverage of the invention further comprises vitamins, minerals, phytate, amino acids and combinations thereof.

In one specific embodiment, the beverages of the invention are calorie-free. In another specific embodiment the beverages of the invention are calcium free.

The invention encompasses methods for management of kidney stone disease in a human in need thereof comprising administration of a beverage comprising a urine citrate increasing component and a urine oxalate reducing component.

In other embodiments, the invention encompasses methods for management of bone disease in a human in need thereof comprising administration of a beverage comprising a urine citrate increasing component and a urine oxalate reducing component.

In one specific embodiment, the beverages in accordance with the invention comprise: 1.0 to 4.0 mmol/L sodium citrate; 3.0 to 7.5 mmol/L potassium citrate; 15 to 25 mmol/L citric acid; 1 to 3 mmol/L magnesium hydroxide; and 1.5-3.5 mg/L pyridoxine, wherein the pH of the beverage is 3.3-7.0.

In another specific embodiment, the beverages in accordance with the invention comprise: 3.33 mmol/L sodium citrate; 5.0 mmol/L potassium citrate; 19.67 mmol/L citric acid; 2.0 mmol/L magnesium hydroxide; and 2.5 mg/L pyridoxine, wherein the pH of the beverage is 3.5.

The invention also encompasses methods for increasing urinary citrate and reducing urinary oxalate by providing a beverage to an individual, said beverage comprising 1 to 4.0 mmol/L sodium citrate; 3.0 to 7.5 mmol/L potassium citrate; 15 to 25 mmol/L citric acid; 1 to 3 mmol/L magnesium hydroxide; and 1.5-3.5 mg/L pyridoxine, wherein the pH of the beverage is 3.3-7.0.

In one specific embodiment, the invention provides a method for increasing urinary citrate and reducing urinary oxalate by providing a beverage to an individual, said beverage comprising 3.33 mmol/L sodium citrate; 5.0 mmol/L potassium citrate; 19.67 mmol/L citric acid; 2.0 mmol/L magnesium hydroxide; and 2.5 mg/L pyridoxine, wherein the pH of the beverage is 3.5.

In another specific embodiment, the invention provides a method for management of kidney stones in a human in need thereof comprising administering a beverage to the human, said beverage comprising 1 to 4.0 mmol/L sodium citrate; 3.0 to 7.5 mmol/L potassium citrate; 15 to 25 mmol/L citric acid; 1 to 3 mmol/L magnesium hydroxide; and 1.5-3.5 mg/L pyridoxine, wherein the pH of the beverage is 3.3-7.0.

In yet another specific embodiment, the invention provides a method for management of kidney stones in a human in need thereof comprising administering a beverage to the human, said beverage comprising 3.33 mmol/L sodium citrate; 5.0 mmol/L potassium citrate; 19.67 mmol/L citric acid; 2.0 mmol/L magnesium hydroxide; and 2.5 mg/L pyridoxine, wherein the pH of the beverage is 3.5.

In another specific embodiment, the invention provides a method management of bone disease in a human in need thereof comprising administering a beverage to the human, said beverage comprising 1 to 4.0 mmol/L sodium citrate; 3.0 to 7.5 mmol/L potassium citrate; 15 to 25 mmol/L citric acid; 1 to 3 mmol/L magnesium hydroxide; and 1.5-3.5 mg/L pyridoxine, wherein the pH of the beverage is 3.3-7.0.

In another specific embodiment, the invention provides a method for management of bone disease in a human in need thereof comprising administering a beverage to the human, said beverage comprising 3.33 mmol/L sodium citrate; 5.0 mmol/L potassium citrate; 19.67 mmol/L citric acid; 2.0 mmol/L magnesium hydroxide; and 2.5 mg/L pyridoxine, wherein the pH of the beverage is 3.5.

The invention also provides a kit comprising a powdered mix, a concentrate, or a tablet comprising:

(a) sodium citrate, potassium citrate, citric acid, magnesium hydroxide, and pyridoxine in amounts such that a beverage prepared from it will have 1.0 to 4.0 mmol sodium citrate, 3.5 to 7.5 mmol potassium citrate, 15 to 25 mmol citric acid, 1 to 3 mmol magnesium hydroxide, and 1.5 to 3.5 mg pyridoxine per liter;
(b) packaging for a container;
(c) a container; and
(d) a set of instructions, said instructions describing how to prepare and store a beverage using the powdered mix or the tablet and describing the frequency and volume of the beverage to be consumed by an individual.

In another specific embodiment, the invention provides a kit comprising a powdered mix, a concentrate, or a tablet comprising:

(a) sodium citrate, potassium citrate, citric acid, magnesium hydroxide, and pyridoxine in amounts such that a beverage prepared from it will have 3.33 mmol sodium citrate, 5.0 mmol potassium citrate, 19.67 mmol citric acid, 2.0 mmol magnesium hydroxide, and 2.5 mg pyridoxine per liter;
(b) packaging for a container;
(c) a container; and
(d) a set of instructions, said instructions describing how to prepare and store a beverage using the powdered mix or the tablet and describing the frequency and volume of the beverage to be consumed by an individual In one embodiment, the invention provides a kit comprising:

(a) a powdered mix, a concentrate, or a tablet comprising sodium citrate, potassium citrate, citric acid, magnesium hydroxide, and pyridoxine in amounts such that a beverage prepared from it will have 1.0 to 4.0 mmol sodium citrate, 3.5 to 7.5 mmol potassium citrate, 15 to 25 mmol citric acid, 1 to 3 mmol magnesium hydroxide, and 1.5 to 3.5 mg pyridoxine per liter;
(b) a set of instructions, said instructions describing how to prepare and store a beverage using the powdered mix, concentrate or the tablet and describing the frequency and volume of the beverage to be consumed by an individual.

In another embodiment, the invention provides a kit comprising (a) a powdered mix, a concentrate, or a tablet comprising sodium citrate, potassium citrate, citric acid, magnesium hydroxide, and pyridoxine in amounts such that a beverage prepared from it will have 3.33 mmol sodium citrate, 5.0 mmol potassium citrate, 19.67 mmol citric acid, 2.0 mmol magnesium hydroxide, and 2.5 mg pyridoxine per liter;
(b) a set of instructions, said instructions describing how to prepare and store a beverage using the powdered mix or the tablet and describing the frequency and volume of the beverage to be consumed by an individual.

In other embodiments, the kit comprises a plurality of portions of powdered mixes, concentrates or tablets and a preselected amount of aqueous liquid (such as water) such that each powdered mix, concentrate or tablet when mixed with the preselected amount of water will provide a beverage as described in the various embodiments herein. Each portion of the powdered mix, concentrate or tablet may be packaged individually in the kit.

The kits of the invention are contemplated to include ready to drink beverages made in accordance with the invention.

Additional aspects and advantages of the invention will be set forth in the description which follows and, in part, will be obvious from the description, or may be learned from practicing the invention as set forth herein. The objects and advantages of the invention will be realized and attained by means of the elements and combinations particularly pointed out herein and specified in the claims. It is to be understood that both the foregoing general description and the following detailed description are exemplary and explanatory and do not restrict the invention as claimed.

BRIEF DESCRIPTION OF THE FIGURES

FIG. 1 is a representation of a scheme for a trial for testing the effect of consumption of a beverage of the present invention.

DETAILED DESCRIPTION OF THE DISCLOSURE

The present disclosure provides a beverage comprising citrate in an amount that delivers clinically significant citrate to individuals such that the occurrence of kidney stones is prevented or reduced. The beverage comprises a urine citrate-increasing component and a urine oxalate-reducing component. Consumption of the beverage raises the urine citrate levels, raises urine pH, and reduces urine oxalate levels. The terms beverage and drink are used interchangeably in this description. In one embodiment, urine citrate and pH are increased, while urine calcium is decreased.

In one embodiment, the urine citrate increasing component comprises, consists essentially of, or consists of sodium citrate, potassium citrate, and citric acid, and the urine oxalate reducing component comprises, consists essentially of, or consists of a magnesium salt (such as magnesium hydroxide) and pyridoxine.

In one embodiment, the beverage of the present disclosure comprises sodium citrate, potassium citrate, citric acid, magnesium hydroxide and pyridoxine. The ingredients are present in such amounts that urine citrate and pH are increased while not altering other urine chemistries. In one embodiment, the citrate may be magnesium citrate instead of or in addition to sodium citrate and potassium citrate. In one embodiment, the citrate comprises, consists essentially of, or consists of potassium citrate and magnesium citrate.

While not intending to be bound by any particular theory, it is considered that the sodium cation improves palatability and also provides a delivery vehicle for high levels of citrate that is not exclusively associated with potassium. In one embodiment, the amount of sodium citrate can be from 0.5 to 5 mmol/L and all amounts therebetween to the tenth decimal place and includes all ranges therebetween. In another embodiment, it is present from 1.0 to 4.0 mmol/L. In another embodiment, it is present from 3.0 to 3.5 mmol/L.

In one embodiment, the beverage is sodium-free. In this embodiment, the beverage may comprise potassium citrate, optionally magnesium citrate, citric acid, magnesium hydroxide, and pyridoxine.

In one embodiment, more potassium is present than sodium. However, the levels of potassium should not be such that it would result in hyperkalemia. In one embodiment, potassium citrate is present from 3.5 to 7.5 mmol/L and all amounts therebetween to the tenth decimal place and includes all ranges therebetween. In another embodiment, it is present from 4.0 to 6.0 mmol/L. In another embodiment it is present from 4.5 to 5.5 mmol/L.

The present beverage also comprises citric acid. In one embodiment, the amount of citric acid is from 15 to 25 mmol/L and all amounts therebetween to the tenth decimal place and includes all ranges therebetween. In another embodiment, the citric acid is present from 17 to 23 mmol/L.

The amount of citrate (calculated from citric acid, sodium citrate, and potassium citrate) is from 20 to 30 mmol/L and all amounts therebetween to the tenth decimal place and includes all ranges therebetween. In one embodiment, the citrate is from 23 to 27 mmol/L.

In one embodiment, the ratio of sodium to potassium is from 1:1.1 to 1:2. In another embodiment, it is from 1:1.3 to 1:1.7. In another embodiment, it is from 1:1.4 to 1:1.6.

To further aid in the prevention or amelioration of kidney stones, the present beverage contains magnesium compounds. Magnesium is a cation that can bind with oxalate in the urine and therefore interfere with the complexing of oxalate with calcium. In one embodiment, the magnesium compound is magnesium hydroxide. In one embodiment, in addition to, or instead of magnesium hydroxide, magnesium citrate may be used. The amount of magnesium hydroxide is from 1 to 3 mmol/L and all amounts therebetween to the tenth decimal place and includes all ranges therebetween. In one embodiment, it is from 1.5 to 2.5 mmol/L.

The present beverage also comprises pyridoxine (Vitamin B6). The amount of pyridoxine is from 1.5 to 3.5 mg/L and all amounts therebetween to the tenth decimal place, and includes all ranges therebetween. In one embodiment, the amount is from 2 to 3 mg/L.

In one embodiment, the beverage of the present invention contains no calcium. In other embodiments, it contains less than 0.1, 0.05 or 0.01 mmol/L of calcium. In one embodiment, the calcium may be higher—i.e., up to 2.5 mmol/L.

The pH of the composition upon mixing of the ingredients is about 3.5. It is generally from 3.4 to 3.7 and all values to the tenth decimal place therebetween. It can be adjusted upward to a pH of from 3.5 to 7.0 and all values to the tenth decimal place therebetween and includes all ranges therebetween. In one embodiment, it is from 3.4 to 4.0.

In one embodiment, the calorie content of the beverage is less than 1. In one embodiment, the caloric content is 0. In another embodiment, the beverage has less than 5 calories (and can therefore, be considered "calorie free"). In another embodiment, it is a low calorie drink. The term "low calorie" as used herein means 40 calories or less. In other embodiments, the caloric content is from 1 to 40 calories and all integers and ranges therebetween. In other embodiments, the drink may have more than 40 calories.

A variety of flavors and/or colors can be added to the beverage as desired. In one embodiment, the color, flavor or other additive does not add any caloric value to the drink and does not alter the sodium, potassium or citrate parameters as described herein. Flavors may be natural or artificial. Examples of suitable flavors include lemon, orange, banana, strawberry, other fruits, fruit punch and the like.

In one embodiment, the composition of the present invention can also include vitamins, minerals, phytate and/or amino acids or other nutrients. Suitable vitamins include vitamin B1, vitamin B2, niacinamide, vitamin B12, folic acid, vitamin C, and vitamin E. Suitable minerals include iron, zinc, vanadium, selenium, chromium, boron, potassium, manganese, copper and magnesium. Suitable amino acids include lysine, isoleucine, leucine, threonine, valine, tryptophan, phenylalanine, methionine and L-selenomethionine. Additionally, wetting agents may also be included to improve mouth feel. In one embodiment, the beverage is a clear drink or a translucent drink.

While not intending to be bound by any particular theory, it is considered that increase in urine citrate and/or the reduction in urinary calcium is obtained, at least in part, due to the "citrate-as-alkali" effect. The organic anions of the present composition are accompanied by positively charged ions (cations) such as sodium or potassium. Therefore, instead of a proton (as would be the case for organic acids like acetic acid or citric acid), the carboxyl yields a bicarbonate without yielding a proton, and leads to net formation of base, which can neutralize other protons in the body, leading to an increase in blood pH and then urine pH and urine citrate. Because blood bicarbonate is readily excreted by the kidneys the pH of the blood changes only slightly while the urine pH will increase. We refer to this as "citrate-as-alkali"—the form of ingested citrate which leads to increased blood pH, urine citrate, urine pH, and therefore to reduction in kidney stone formation.

In one embodiment, other agents may be added that contribute to increasing the urinary pH. For example, malate or organic anions can be added.

In one embodiment, the present beverage may contain agents which can enhance the flavor or appearance of the beverage, but which do not affect the citrate or oxalate content of the urine or the ratio of sodium to potassium. These agents are referred to herein as "non-active" agents. In one embodiment, the non-active agents do not change the sodium or potassium content. In one embodiment, the non-active agents do not change the sodium or potassium content by more than 0.1%.

The beverage can be packaged in suitable containers such as bottles, cans, cardboard packages or the like in any suitable size including up to 0.5, 1 or 2 liter portions. The beverages can be aseptically packaged and stored at ambient temperatures (generally from 65 to 75 F) or at refrigeration temperatures.

In one embodiment, instead of a beverage, all of the above formulations can be provided in the form of powdered mixes, concentrated liquid (concentrate) or tablets. In one embodiment, the present invention provides a kit comprising a powdered mix, concentrated liquid or a tablet, which upon mixing with a suitable liquid (such as water) or diluting (if it is concentrate), will provide the beverage of the present invention. The kit may also contain a set of instruction for preparing the beverage from the powdered mix, concentrate or the tablet and for consumption (such as over a 24 hour period). The set of instructions may provide the frequency and the amount of beverage to be consumed over a 24 hour (or other selected) period. The set of instructions may also provide storage recommendations. The powdered mix, concentrate and the tablets can be packaged in suitable containments—such as paper packages or pouches for the powdered mix, cartons, bottles, containers, or boxes for the concentrate, and blister packages for tablets. The powdered mix, concentrate or the tablet can be portioned such that they can be made into a preselected volume of beverage. For example, the powdered mix, concentrate or the tablet can be portioned such that it makes up a quart, half liter or a liter of beverage. Further, a kit may contain multiple pouches of the powdered mix and one or more sheets of the blister packaged tablet. The term tablets includes any compacted form of the powdered formulation including pills, caplets and the like. The kit may also contain the liquid for making up the beverage. For example, the kit may contain a measured amount of liquid for adding the powdered mix, concentrate or the tablet. Packaging can be compartmentalized such that the powdered mix, concentrate or the tablet is in one compartment and a measured amount of liquid in the other. The partition between these compartments may be such that it can be pierced or removed with or without exposing the contents to the outside thereby allowing mixing of the contents of the two compartments. The packaging can be in suitable portions allowing packing together of the supply for a day or a week or a month etc.

In one embodiment, the beverage of the present disclosure provides a calorie-free and calcium-free beverage. One to 2 liters of the beverage can be conveniently consumed over a 24 hour period to increase urinary citrate levels and reduce urinary oxalate levels, while not affecting other chemistries. This drink will be useful for individuals who have been diagnosed with kidney stones, for individuals who are at risk for developing stones, and generally for any individual for the prevention of kidney stones. This drink is also useful for general consumption such as a thirst quencher. The beverage may be consumed by humans—both adults and children of all ages. It may also be used for consumption by animals. It may be used by individuals who are in need of increasing urine citrate levels, raising urine pH, or reducing urine oxalate levels. It may also be used by individuals with no known diagnosed disease conditions or by individuals having disease conditions (whether diagnosed or not) including individuals with bone diseases.

In one embodiment, the present disclosure provides a beverage which is organoleptically acceptable to consumers, and in a 1 liter package/container provides to the consumer from 1 to 4 mmol of sodium citrate, 4 to 6 mmol of potassium citrate, 15 to 25 mmol of citric acid, 1.5 to 3.5 mg of pyridoxine, and 1 to 3 mmol of magnesium hydroxide. In one embodiment, the 1 liter beverage does not contain any other salts. In one embodiment, the 1 liter beverage does not contain any other sodium or potassium salts or any other citrate, and does not contain any other agent that would alter the amount of oxalate in the urine. Non-active agents like color and flavors may be added to the beverage. The beverage may be calorie-free, low calorie or may provide more than 40 calories.

In another embodiment, the present disclosure provides a beverage which is organoleptically acceptable to consumers, and in a 1 liter package/container provides to the consumer from 3 to 3.5 mmol of sodium citrate, 4.5 to 5.5 mmol of potassium citrate, 18 to 22 mmol of citric acid, 2 to 3 mg of pyridoxine, and 1.5 to 2.5 mmol of magnesium hydroxide. In one embodiment, the 1 liter beverage does not contain any other sodium or potassium salts or any other citrate, and does not contain any other agent that would alter the amount of oxalate in the urine. However, non-active agents like color and flavors may be added to the beverage. The beverage may be calorie-free, low calorie or may provide more than 40 calories.

The present disclosure also provides a method for preventing or reducing the occurrence of kidney stones. The method comprises providing to an individual a beverage of the present invention in an amount that is sufficient to reduce or prevent the formation of kidney stones. It is considered that the present beverage alters urine composition to make the urine less hospitable for kidney stone formation, by raising urine citrate and urine pH. The present beverage also lowers urine oxalate levels. In one embodiment, an individual consumes from 1 to 2 liters of the beverage per day (24 hour period).

The present compositions may also be used to improve bone mineral density and therefore, for the treatment, prevention or reduction of osteoporosis, osteopenia and metastatic bone cancer. In one embodiment, the compositions may be used in the treatment, prevention or reduction of chronic renal insufficiency.

In one embodiment, the beverage may contain from, 0.1% to 10% sweeteners and all percentages to the tenth decimal place therebetween. The sweeteners may be nutritive and non-nutritive, natural and artificial or synthetic. Such sweeteners are well known in the art.

In some aspects and embodiments, the present disclosure provides the following:

A calorie-free, calcium-free beverage consisting essentially of a urinary citrate increasing component and a urinary oxalate reducing component.

A calorie free, calcium free beverage consisting essentially of 1.0 to 4.0 mmol/L sodium citrate, 3.5 to 7.5 mmol/L potassium citrate, 15 to 25 mmol/L citric acid, 1 to 3 mmol/L magnesium hydroxide, and 1.5 to 3.5 mg/L pyridoxine, wherein the pH of the beverage is from 3.3 to 7.0.

A method for increasing urinary citrate and reducing urinary oxalate by providing a beverage to an individual, said beverage essentially consisting of 1.0 to 4.0 mmol/L sodium citrate, 3.5 to 7.5 mmol/L potassium citrate, 15 to 25 mmol/L citric acid, 1 to 3 mmol/L magnesium hydroxide, and 1.5 to 3.5 mg/L pyridoxine, wherein the pH of the beverage is from 3.3 to 7.0.

A method of preventing or reducing the occurrence of kidney stones by providing a beverage to an individual, said beverage comprising a urinary citrate increasing component and a urinary oxalate reducing component, wherein said beverage in a volume of 1-2 liters is consumed by the individual over a 24 hour period.

A kit comprising a powdered mix a concentrate or a tablet comprising sodium citrate, potassium citrate, citric acid, magnesium hydroxide, and pyridoxine in amounts such that a beverage prepared from it will have 1.0 to 4.0 mmol sodium citrate, 3.5 to 7.5 mmol potassium citrate, 15 to 25 mmol citric acid, 1 to 3 mmol magnesium hydroxide, and 1.5 to 3.5 mg pyridoxine per liter, packaged in a containment, and a set of instructions, said instructions describing how to prepare and store a beverage using the powdered mix or the tablet and describing the frequency and volume of the beverage to be consumed by an individual.

Examples of some specific embodiments of this disclosure are provided below:

A beverage comprising a urine citrate increasing component and a urine oxalate reducing component.

A beverage comprising a urine citrate increasing component and a urine oxalate reducing component, wherein the urine citrate increasing component comprises sodium citrate.

A beverage comprising a urine citrate increasing component and a urine oxalate reducing component, wherein the urine citrate increasing component comprises potassium citrate.

A beverage comprising a urine citrate increasing component and a urine oxalate reducing component, wherein the urine citrate increasing component comprises magnesium citrate.

A beverage comprising a urine citrate increasing component and a urine oxalate reducing component wherein the urine citrate increasing component is selected from the group consisting of sodium citrate, potassium citrate, magnesium citrate and combinations thereof.

A beverage comprising sodium citrate, potassium citrate, magnesium citrate, citric acid, pyridoxine and combinations thereof.

A beverage comprising a urine citrate increasing component and a urine oxalate reducing component, wherein the oxalate reducing component is a magnesium salt.

A beverage comprising a urine citrate increasing component and a urine oxalate reducing component, wherein the oxalate reducing component is a magnesium salt and wherein the magnesium salt is magnesium hydroxide.

A beverage comprising a urine citrate increasing component and a urine oxalate reducing component, wherein the oxalate reducing component is selected from the group consisting of a magnesium, pyridoxine and combinations thereof.

A beverage comprising a urine citrate increasing component and a urine oxalate reducing component, and further comprising vitamins, minerals, phytate, amino acids and combinations thereof.

A calorie-free beverage comprising a urine citrate increasing component and a urine oxalate reducing component.

A calcium-free beverage comprising a urine citrate increasing component and a urine oxalate reducing component.

A method for management of kidney stone disease in a human in need thereof comprising administration of a beverage comprising a urine citrate increasing component and a urine oxalate reducing component.

A method for management of bone disease in a human in need thereof comprising administration of a beverage comprising a urine citrate increasing component and a urine oxalate reducing component.

A beverage comprising citrate, magnesium, and pyridoxine.

A beverage comprising citrate, magnesium, and pyridoxine, wherein the source of citrate ions is selected from the group consisting of sodium citrate, potassium citrate, magnesium citrate and combinations thereof.

A beverage comprising citrate, magnesium, and pyridoxine, wherein the source of magnesium is magnesium hydroxide or magnesium citrate.

A beverage comprising:

(1) 1.0 to 4.0 mmol/L sodium citrate;

(2) 3.0 to 7.5 mmol/L potassium citrate;

(3) 15 to 25 mmol/L citric acid;

(4) 1 to 3 mmol/L magnesium hydroxide; and (5) 1.5-3.5 mg/L pyridoxine wherein the pH of the beverage is 3.3-7.0.

A beverage comprising:

(1) 3.33 mmol/L sodium citrate (2) 5.0 mmol/L potassium citrate;

(3) 19.67 mmol/L citric acid;

(4) 2.0 mmol/L magnesium hydroxide; and (5) 2.5 mg/L pyridoxine wherein the pH of the beverage is 3.5.

A beverage comprising: 1.0 to 4.0 mmol/L sodium citrate; 3.0 to 7.5 mmol/L potassium citrate; 15 to 25 mmol/L citric acid; 1 to 3 mmol/L magnesium hydroxide; and 1.5-3.5 mg/L pyridoxine, wherein the pH of the beverage is 3.3-7.0 and wherein the beverage is calcium-free.

A beverage comprising: 1.0 to 4.0 mmol/L sodium citrate; 3.0 to 7.5 mmol/L potassium citrate; 15 to 25 mmol/L citric acid; 1 to 3 mmol/L magnesium hydroxide; and 1.5-3.5 mg/L pyridoxine, wherein the pH of the beverage is 3.3-7.0 and wherein the beverage is calorie-free.

A beverage comprising 3.33 mmol/L sodium citrate; 5.0 mmol/L potassium citrate; 19.67 mmol/L citric acid; 2.0 mmol/L magnesium hydroxide; and 2.5 mg/L pyridoxine, wherein the pH of the beverage is 3.5 and wherein the beverage is calcium-free.

A beverage comprising 3.33 mmol/L sodium citrate; 5.0 mmol/L potassium citrate; 19.67 mmol/L citric acid; 2.0 mmol/L magnesium hydroxide; and 2.5 mg/L pyridoxine, wherein the pH of the beverage is 3.5 and wherein the beverage is calorie-free.

A method for increasing urinary citrate and reducing urinary oxalate by providing a beverage to an individual, said beverage comprising 1 to 4.0 mmol/L sodium citrate; 3.0 to 7.5 mmol/L potassium citrate; 15 to 25 mmol/L citric acid; 1 to 3 mmol/L magnesium hydroxide; and 1.5-3.5 mg/L pyridoxine, wherein the pH of the beverage is 3.3-7.0.

A method for increasing urinary citrate and reducing urinary oxalate by providing a beverage to an individual, said beverage comprising 3.33 mmol/L sodium citrate; 5.0 mmol/L potassium citrate; 19.67 mmol/L citric acid; 2.0 mmol/L magnesium hydroxide; and 2.5 mg/L pyridoxine, wherein the pH of the beverage is 3.5.

A method for management of kidney stones in a human in need thereof comprising administering a beverage to the human, said beverage comprising 1 to 4.0 mmol/L sodium citrate; 3.0 to 7.5 mmol/L potassium citrate; 15 to 25 mmol/L citric acid; 1 to 3 mmol/L magnesium hydroxide; and 1.5-3.5 mg/L pyridoxine, wherein the pH of the beverage is 3.3-7.0.

A method for management of kidney stones in a human in need thereof comprising administering a beverage to the human, said beverage comprising 3.33 mmol/L sodium citrate; 5.0 mmol/L potassium citrate; 19.67 mmol/L citric acid; 2.0 mmol/L magnesium hydroxide; and 2.5 mg/L pyridoxine, wherein the pH of the beverage is 3.5.

A method for management of bone disease in a human in need thereof comprising administering a beverage to the human, said beverage comprising 1 to 4.0 mmol/L sodium citrate; 3.0 to 7.5 mmol/L potassium citrate; 15 to 25 mmol/L citric acid; 1 to 3 mmol/L magnesium hydroxide; and 1.5-3.5 mg/L pyridoxine, wherein the pH of the beverage is 3.3-7.0

A method for management of bone disease in a human in need thereof comprising administering a beverage to the human, said beverage comprising 3.33 mmol/L sodium citrate; 5.0 mmol/L potassium citrate; 19.67 mmol/L citric acid; 2.0 mmol/L magnesium hydroxide; and 2.5 mg/L pyridoxine, wherein the pH of the beverage is 3.5.

A kit comprising a powdered mix a concentrate or a tablet comprising:

(a) sodium citrate, potassium citrate, citric acid, magnesium hydroxide, and pyridoxine in amounts such that a beverage prepared from it will have 1.0 to 4.0 mmol sodium citrate, 3.5 to 7.5 mmol potassium citrate, 15 to 25 mmol citric acid, 1 to 3 mmol magnesium hydroxide, and 1.5 to 3.5 mg pyridoxine per liter;

(b) packaging for a container;

(c) a container; and (d) a set of instructions, said instructions describing how to prepare and store a beverage using the powdered mix or the tablet and describing the frequency and volume of the beverage to be consumed by an individual.

A kit comprising a powdered mix a concentrate or a tablet comprising:

(a) sodium citrate, potassium citrate, citric acid, magnesium hydroxide, and pyridoxine in amounts such that a beverage prepared from it will have 3.33 mmol sodium citrate, 5.0 mmol potassium citrate, 19.67 mmol citric acid, 2.0 mmol magnesium hydroxide, and 2.5 mg pyridoxine per liter;

(b) packaging for a container;

(c) a container; and (d) a set of instructions, said instructions describing how to prepare and store a beverage using the powdered mix or the tablet and describing the frequency and volume of the beverage to be consumed by an individual.

A beverage concentrate comprising a urine citrate increasing component and a urine oxalate reducing component.

A beverage concentrate comprising a urine citrate increasing component and a urine oxalate reducing component wherein the urine increasing component is selected from the group consisting of sodium citrate, potassium citrate, magnesium citrate and combinations thereof.

The following examples are provided as illustrative examples and are not intended to be restrictive in any way.

EXAMPLE 1

This example provides results obtained from ingestion of the beverage on urine composition. A placebo controlled trial was performed in which 24 hour urine samples were collected while drinking 2 L of water (placebo) and then a subsequent 24-hour urine sample was collected while drinking 2 L of the present beverage. The protocol followed for the trial is shown in FIG. 1. The Washout phase is between the placebo phase and the experimental phase. During the washout phase, the diet was ad lib (meaning the individuals consumed what they wanted.). The beverage had the following composition.

Sodium Citrate 3.33 mmol/liter
Potassium Citrate 5.0 mmol/liter
Citric Acid 19.67 mmol/liter
$Mg(OH)_2$ 2.0 mmol/liter
Pyridoxine 2.5 mg/liter The pH of the composition was 3.5. Ten participants have completed the trial and for each, significant increase in pH, citrate, and potassium and significant decrease in calcium and supersaturation of uric acid (SSUA) was observed. Data (average values) are provided in the table below.

| Urine Parameter | Placebo | Present formulation | Statistical significance |
|---|---|---|---|
| Calcium | 206.1 mg/day | 158.6 mg/day | 0.04 |
| Citrate | 616.4 mg/day | 945.1 mg/day | <0.0001 |
| pH | 6.33 | 6.97 | 0.0003 |
| Supersaturation of uric acid (SSUA) | 0.37 | 0.12 | 0.02 |
| Potassium | 74.7 mEq/day | 96.7 mEq/day | 0.001 |

It is considered that the increase in citrate and decrease in calcium both indicate that the drink decreases the likelihood of producing a calcium oxalate stone if given to a calcium stone former. The increase in pH and the decrease in SSUA indicate that the drink decreases the likelihood of making a uric acid stone if given to a uric acid stone former. The increase in pH indicates that the drink decreases the likelihood of producing a cystine stone if given to a cystine stone former. The increase in potassium indicates that the participants did “absorb” the potassium in the drink and were compliant during the trial (If they didn’t drink the drink in the right amounts, the potassium would not have changed).

What is claimed is:

1. A method of reducing the formation of kidney stones in a subject who is afflicted with kidney stones, said method comprising administering to the subject 1 to 2 liters of a beverage over a period of 24 hours, said beverage comprising sodium citrate, potassium citrate, citric acid, magnesium salt and pyridoxine, wherein the magnesium salt is magnesium citrate or magnesium hydroxide.

2. The method of claim 1, wherein the pH of the beverage is from 3.4 to 3.7.

3. The method of claim 1, wherein the beverage comprises:

(1) 1.0 to 4.0 mmol/L sodium citrate;
(2) 3.0 to 7.5 mmol/L potassium citrate;
(3) 15 to 25 mmol/L citric acid;
(4) 1 to 3 mmol/L magnesium hydroxide; and
(5) 1.5-3.5 mg/L pyridoxine, and wherein the pH of the beverage is 3.3-7.0.

4. The method of claim 1, wherein the beverage is calorie-free, calcium-free, or both calorie-free and calcium-free.

5. A method of reducing the formation of kidney stones in a subject who is afflicted with kidney stones, said method comprising administering to the subject 1 to 2 liters of a beverage over a period of 24 hours, said beverage comprising 1.0 to 4.0 mmol/L sodium citrate; 3.0 to 7.5 mmol/L potassium citrate; 15 to 25 mmol/L citric acid; and 1 to 3 mmol/L magnesium hydroxide.

6. The method of claim 5, wherein the pH of the beverage is from 3.4 to 3.7.

7. A method of reducing the formation of kidney stones in a subject who is afflicted with kidney stones, said method comprising administering to the subject 1 to 2 liters of a beverage over a period of 24 hours, said beverage comprising sodium citrate, potassium citrate, citric acid, and magnesium salt, wherein the magnesium salt is magnesium citrate or magnesium hydroxide and wherein the beverage is calorie-free, calcium-free or both calcium-free and calorie-free.

8. The method of claim 7, wherein the pH of the beverage is from 3.4 to 3.7.

* * * * *